(12) United States Patent
Jozwik et al.

(10) Patent No.: US 10,994,071 B2
(45) Date of Patent: May 4, 2021

(54) SYRINGE ADAPTER WITH CONCENTRIC RINGS

(71) Applicant: ILLINOIS TOOL WORKS INC., Glenview, IL (US)

(72) Inventors: Raymond Jozwik, Hendersonville, TN (US); Michael G. Leonhard, West Bend, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 772 days.

(21) Appl. No.: 15/117,745

(22) PCT Filed: Feb. 13, 2015

(86) PCT No.: PCT/US2015/015912
§ 371 (c)(1),
(2) Date: Aug. 10, 2016

(87) PCT Pub. No.: WO2015/123577
PCT Pub. Date: Aug. 20, 2015

(65) Prior Publication Data
US 2016/0354537 A1    Dec. 8, 2016

Related U.S. Application Data

(60) Provisional application No. 61/940,550, filed on Feb. 17, 2014.

(51) Int. Cl.
*A61M 5/00* (2006.01)
*A61M 5/145* (2006.01)
(Continued)

(52) U.S. Cl.
CPC ........ *A61M 5/007* (2013.01); *A61M 5/14546* (2013.01); *A61M 5/14566* (2013.01);
(Continued)

(58) Field of Classification Search
CPC .............. A61M 5/14546; A61M 5/007; A61M 5/14566; A61M 2005/3114; A61M 2005/31588
See application file for complete search history.

(56) References Cited

U.S. PATENT DOCUMENTS

| | | | |
|---|---|---|---|
| 2003/0040719 A1 | 2/2003 | Spohn et al. | |
| 2010/0198060 A1* | 8/2010 | Fago ................. | A61M 5/14546 600/432 |
| 2011/0144486 A1* | 6/2011 | Bruce ............... | A61M 5/14546 600/432 |

FOREIGN PATENT DOCUMENTS

| | | | |
|---|---|---|---|
| JP | 2011224273 A | 11/2011 | |
| WO | 9736635 A1 | 10/1997 | |

(Continued)

OTHER PUBLICATIONS

ISR and WO for PCT/US2015/015912 dated May 7, 2015.

*Primary Examiner* — Nathan R Price
*Assistant Examiner* — Melissa A Snyder
(74) *Attorney, Agent, or Firm* — Pauley Erickson & Swanson

(57) ABSTRACT

An adapter for use with a syringe and a power injector includes an outer ring having a first end configured for passage of an end of a syringe having at least one flange. An inner ring is disposed coaxially within the outer ring. The inner ring has a first end including at least one flange slot. A magnet fixed relative to the inner ring such that when the syringe end is disposed in the outer ring and the at least one flange engages the at least one flange slot, rotation of the syringe causes rotation of the inner ring and magnet relative to the outer ring.

20 Claims, 8 Drawing Sheets

(51) Int. Cl.
*A61M 5/20* (2006.01)
*A61M 5/31* (2006.01)
*A61M 5/315* (2006.01)

(52) U.S. Cl.
CPC ............ *A61M 5/20* (2013.01); *A61M 5/3135* (2013.01); *A61M 5/31578* (2013.01); *A61M 5/31515* (2013.01); *A61M 2005/3114* (2013.01); *A61M 2005/31588* (2013.01)

(56) References Cited

FOREIGN PATENT DOCUMENTS

| | | |
|---|---|---|
| WO | 2009045714 A1 | 4/2009 |
| WO | 2010021953 A2 | 2/2010 |

\* cited by examiner

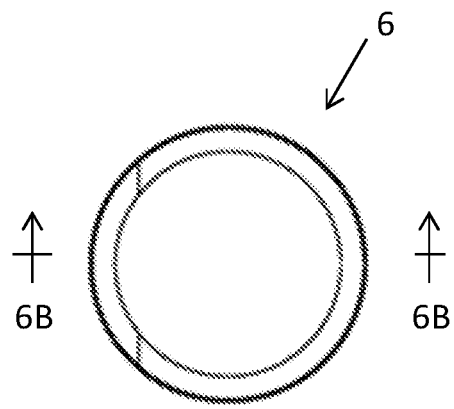
FIG. 6A
FIG. 6B
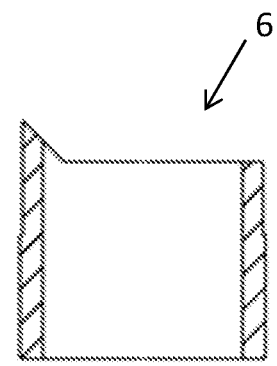
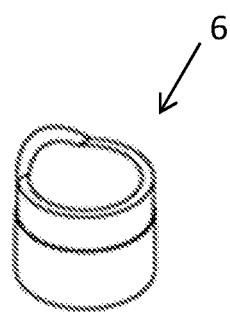
FIG. 6C

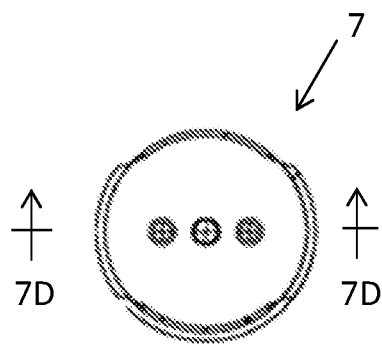
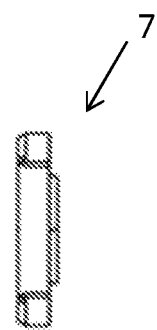
FIG. 7A  FIG. 7B
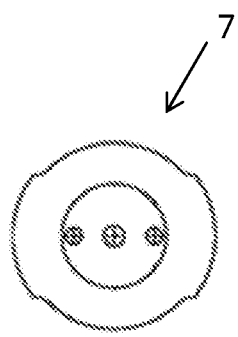
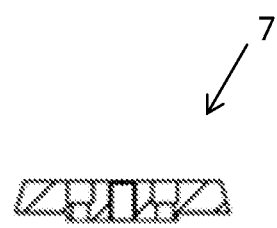
FIG. 7C  FIG. 7D
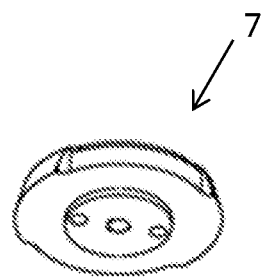
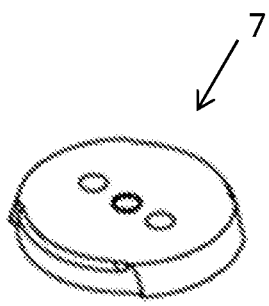
FIG. 7E  FIG. 7F

SYRINGE ADAPTER WITH CONCENTRIC RINGS

CROSS-REFERENCE TO RELATED APPLICATIONS

This application is National Phase of International Application No. PCT/US2015/015912 filed Feb. 13, 2015 and claims the benefit of and priority to U.S. Provisional Application No. 61/940,550, filed Feb. 17, 2014.

BACKGROUND

This invention relates in general to syringes and syringe adapters used in conjunction with power injectors.

Injectors are devices that expel fluid, such as contrast fluid, into a circulatory system, which is used to enhance medical imaging like, for example, x-ray or magnetic imaging. The contrast fluid or contrast media is injected from a syringe, through a tube, and into an animal subject or human patient. Injectors are well known for use with a powered injector unit that is frequently fixed to a stand or support. Injectors typically include a plunger drive that couples to the plunger of the syringe and moves the plunger forward to expel fluid into the tube thereby injecting the contrast media in the subject.

Powered injectors or motorized injectors often include circuitry that controls the plunger drive unit for setting the rate of injection and/or the amount of fluid injected. Typically, the control circuitry includes switches which allow a user to manually actuate the drive unit to move the plunger within the syringe. The injector may cycle the plunger through the syringe one or more times to fill the syringe with fluid and expel any air bubbles trapped inside. Other syringes come pre-filled, which reduces the number of plunger drive movements needed to prepare the injector for a new injection. After the procedure has ended, the syringe plunger, typically positioned at the forward end of the syringe barrel, is retracted so that the syringe may be removed from the injector. In some injectors, the syringe can only be removed or replaced while the plunger drive is fully retracted.

Excess contrast media remaining in a syringe after an injection must be discarded as is well known in medical procedures to prevent cross contamination and/or infection. However, contrast media can be expensive. For this reason, when preparing for an injection, an empty syringe is filled with only as much media as will be needed for the next procedure. Similarly, pre-filled syringes are sold in a number of sizes, for example ranging from 60 to 200 milliliters, allowing the operator preparing for an injection to select a syringe containing only as much media as is needed for that procedure. Accordingly, the syringes may have one or more characteristic properties or parameters that if communicated to the power injector would assist the operator in the procedure and provide safeguards for ensuring proper use of the contrast media. Examples of such parameters may include syringe diameter or length, syringe material, contrast fluid composition and concentration of the contrast media. These parameters may affect certain procedures like the delivery rate or pressure.

In some situations, customized syringes are intended to be used with certain specific power injectors.

SUMMARY

This invention relates more specifically to a syringe adapter that allows for the safe and effective use of non OEM syringes on power injectors that are used to deliver contrast and other diagnostic fluids during imaging procedures; in particular, an adapter utilizing two concentric rings.

In at least one embodiment, a magnet fixed to an inner rotating ring may be driven to a position that may make certain indications to an injector, such the load or lock state of a syringe. In further embodiments, it may be that the magnet that is fixed to the inner rotating ring interacts with a hall effect sensor of the injector to signal that the syringe is loaded/unloaded and/or locked/unlocked, thus indicating that the syringe is in a certain position and ready for subsequent phases of an injection procedure Various aspects will become apparent to those skilled in the art from the following detailed description and the accompanying drawings.

BRIEF DESCRIPTION OF THE DRAWINGS

FIG. 6A is a top view of the ram sleeve of FIG. 1.

FIG. 6B is a cross-sectional view of the ram sleeve of FIG. 6A taken along line 6B.

FIG. 6C is a perspective view of the ram sleeve of FIG. 6A.

FIG. 7A is a top view of the ram tip of FIG. 1.

FIG. 7B is a side view of the ram tip of FIG. 7A.

FIG. 7C is a bottom view of the ram tip of FIG. 7A.

FIG. 7D is a cross-sectional view of the ram tip of FIG. 7A taken along line 7D.

FIG. 7E is a bottom perspective view of the ram tip of FIG. 7A.

FIG. 7F is a top perspective view of the ram tip of FIG. 7A.

DETAILED DESCRIPTION

Figure 1:
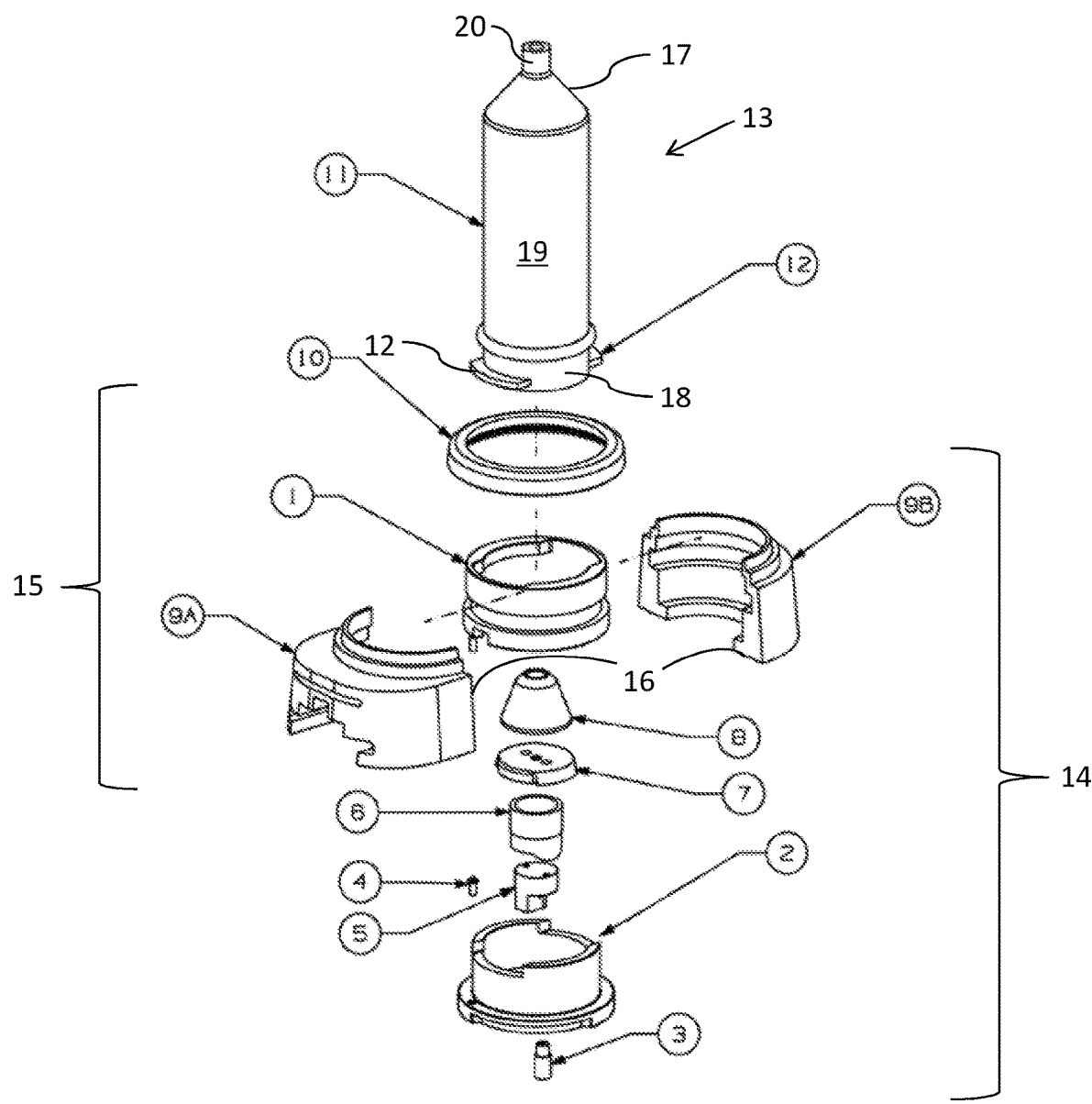
FIG. 1 is an exploded view of a portion of an injector assembly including an adapter and a syringe.
Figure 2A:
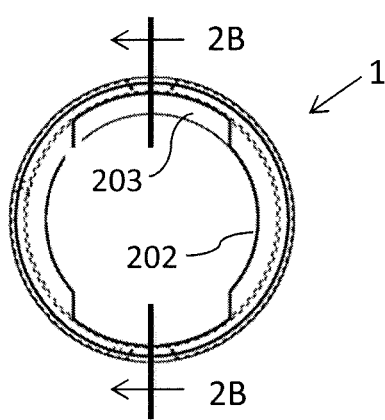
FIG. 2A is a top view of the outer ring of FIG. 1.
Figure 2B:
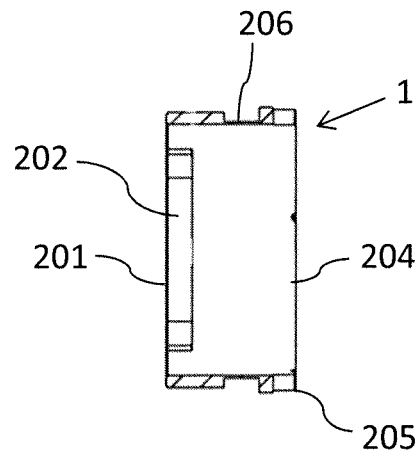
FIG. 2B is a side cross-sectional view of the outer ring of FIG. 2A taken along line 2B.
Figure 2C:
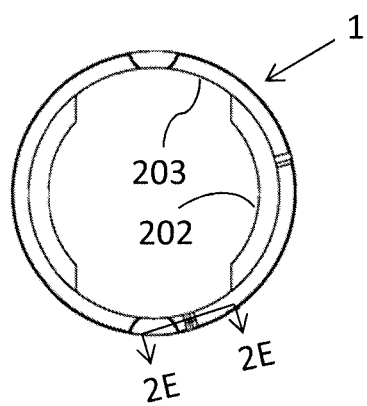
FIG. 2C is a bottom view of the outer ring of FIG. 2A.
Figure 2D:
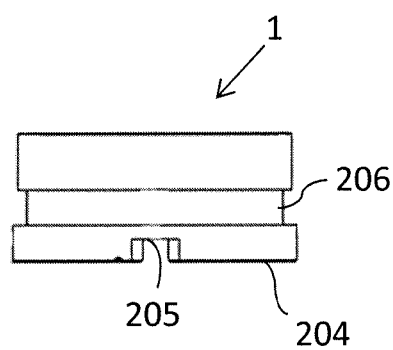
FIG. 2D is a side view of the outer ring of FIG. 2A.
Figure 2E:
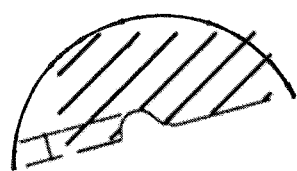
FIG. 2E is a partial cross-sectional view of the outer ring of FIG. 2C taken along line 2E.
Figure 2F:
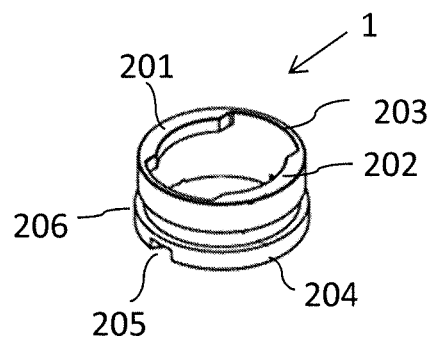
FIG. 2F is a perspective view of the outer ring of FIG. 2A.
Figure 3A:
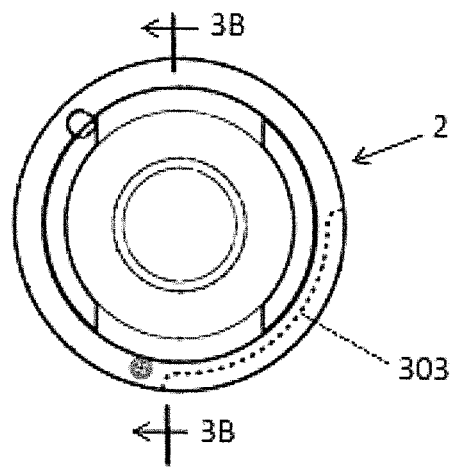
FIG. 3A is top view of the inner ring of FIG. 1.
Figure 3B:
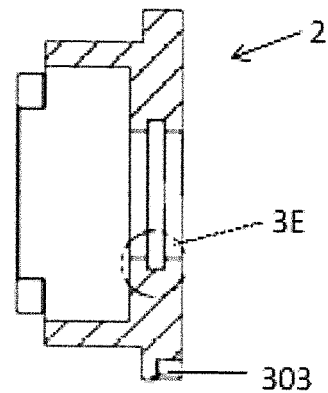
FIG. 3B is a side cross-sectional view of the inner ring of FIG. 3A taken along line 3B.
Figure 3C:
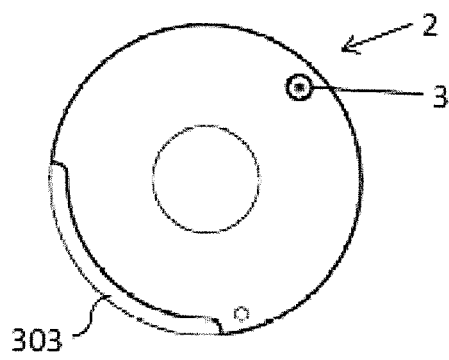
FIG. 3C is a bottom view of the inner ring of FIG. 3A.
Figure 3D:
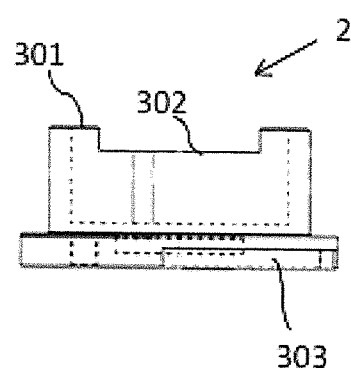
FIG. 3D is a side view of the inner ring of FIG. 3A.
Figure 3E:
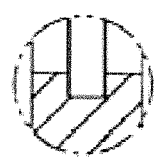
FIG. 3E is an enlarged portion of the inner ring of FIG. 3B at 3E.
Figure 3F:
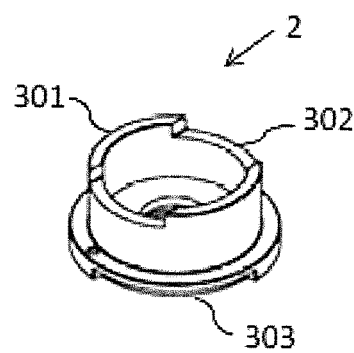
FIG. 3F is a perspective view of the inner ring of FIG. 3A.
Figure 4A:
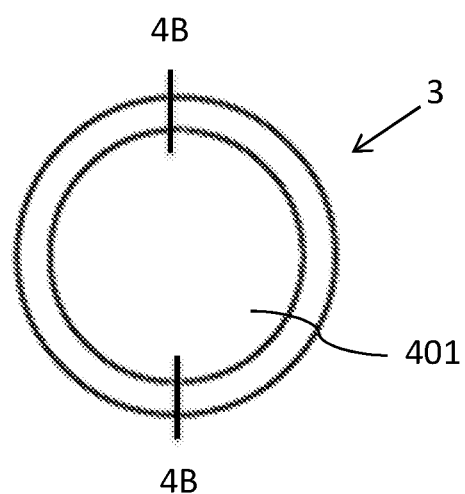
FIG. 4A is an end view of the magnet holder of FIG. 1.
Figure 4B:
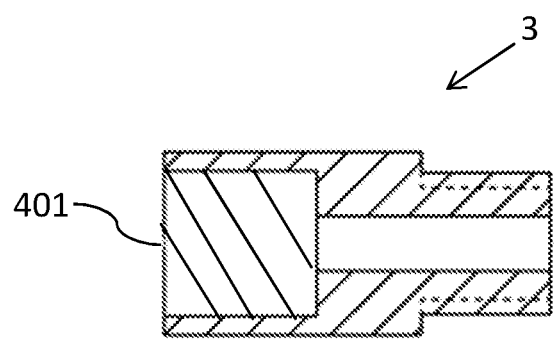
FIG. 4B is a side cross-sectional view of the magnet holder of FIG. 4A taken along line 4B.
Figure 5A:
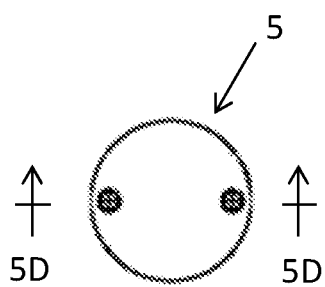
FIG. 5A is a top view of the ram extension of FIG. 1.
Figure 5B:
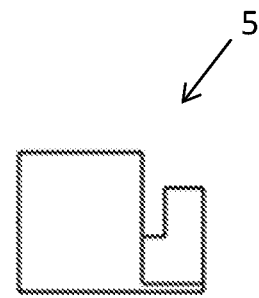
FIG. 5B is a side view of the ram extension of FIG. 5A.
Figure 5C:
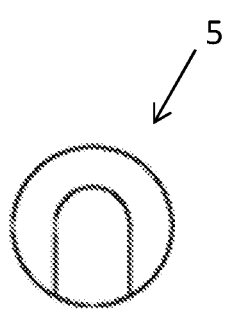
FIG. 5C is a bottom view of the ram extension of FIG. 5A.
Figure 5D:
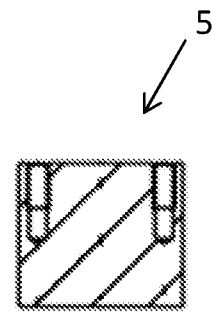
FIG. 5D is a front cross-sectional view of the ram extension of FIG. 5A taken along line 5D.
Figure 5E:
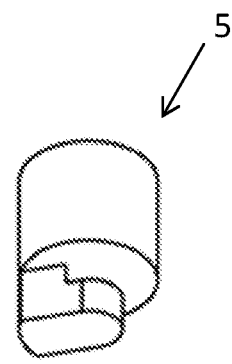
FIG. 5E is a bottom perspective view of the ram extension of FIG. 5A.
Figure 5F:
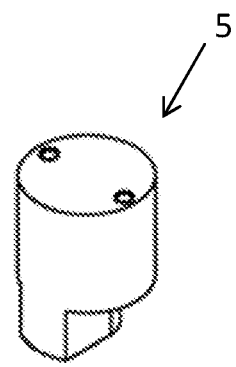
FIG. 5F is a top perspective view of the ram extension of FIG. 5A.
Figure 8A:
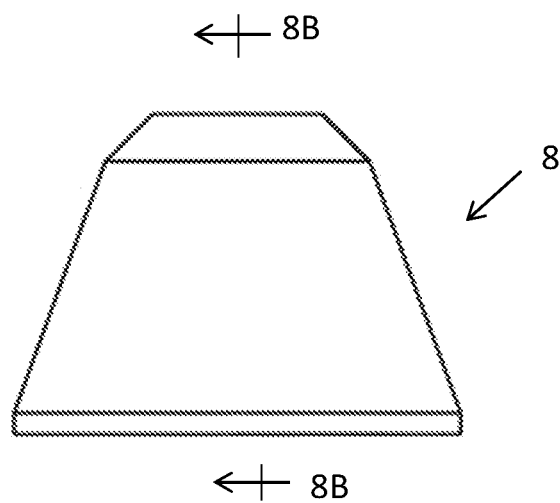
FIG. 8A is a side view of the cone of FIG. 1.
Figure 8B:
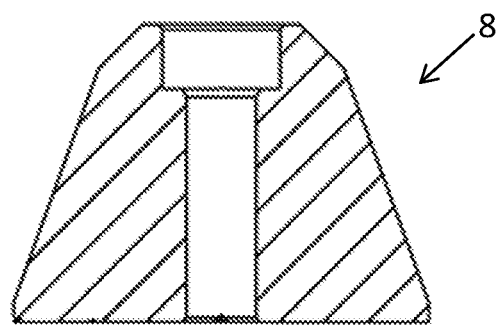
FIG. 8B is a cross-sectional view of the cone of FIG. 8A taken along line 8B.

Referring now to the drawings collectively, there is illustrated a portion of an power injector assembly 15 with an adapter 14 and a syringe 13, together forming part of a medical system for injecting a fluid.

The adapter 14 includes an outer ring 1 and a concentric inner ring 2 which is coaxially disposed with the outer ring 1.

The outer ring 1 has a first end 201 configured for passage of an end of a syringe having at least one flange. As illustrated the first end 201 includes one or more ring flanges 202 that define recesses 203 for passage of syringe flanges, as will be further discussed below. The outer ring 1 includes a second end 204 having a slot 205 for engagement of a protrusion on the faceplate 16 of the injector 15. For example, the injector 15 may include a spring plunger 4 for engaging the slot 205 in the outer ring 1 for biasing the position of the inner ring 1 relative to the faceplate 16.

Further an annular groove 206 may be disposed between the first end 201 and the 204 for cooperative engagement with the faceplate 16.

The inner ring 2 is disposed coaxially within the outer ring 1. The inner ring 2 has a first end 301 including one or more flange slots 302.

The inner ring 2 may include a partially circumscribed radial slot 303 for interaction with a protrusion on a head (not shown) of the injector 15 to limit rotation of the inner ring 2 relative to the injector head.

A magnet 401 is fixed relative to the inner ring 2 by a magnet holder 3, the operation of which will be further described below.

The injector assembly 15 includes a faceplate 16 having an upper faceplate portion 9B and a lower faceplate portion 9A that together are disposed about the outer ring 1 and retain the adapter 14 to the injector assembly 15. The injector 15 further includes a faceplate ring 10 that cooperates with the upper faceplate portion 9B and the lower faceplate portion 9A to retain the outer ring 1 within the faceplate 16.

The illustrated syringe 13 has a barrel 11 having a distal end 17 and a proximal end 18 an interior volume 19 is defined therebetween. There are one or more syringe flanges 12 extending from the proximal end 18. A delivery tip 20 extends from the distal end 17.

The power injector assembly 15 includes a ram (not shown) for pushing fluid from the syringe 13.

In operation, a plunger (not shown) is disposed within the barrel 11 and may be driven by the ram of the injector assembly 15. The ram may drive the plunger to push fluid from the syringe 13.

The injector assembly may also optionally include a ram extension 5 connected to the end of the ram to accommodate a variety of syringe designs and/or use of an adapter to thus account for any difference in ram stroke length/position due to use of syringes of differing designs and/or the use of an adapter. A ram tip 7 may be connected to the end of the ram extension 5 opposite the ram, and a cone 8, for supporting the plunger, may be connected to the ram tip 8 opposite the ram extension 7. An optional ram sleeve 6 may be disposed about the ram extension 5, as desired.

In operation of the illustrated example, the inner ring 2 has two flange slots 302 in opposed position about the circumference of the first end 301 and the syringe 13 has two flanges 12 extending in opposed directions from the circumference of the proximal end 18 of the barrel 11. During placement of the syringe 13, the proximal end 18 is moved through the first end 201 of the outer ring 1 with the syringe flanges 12 passing through the recess 203. The two syringe flanges 12 are placed in the flange slots 302 of the inner ring 2.

Once the proximal end 18 of the syringe 13 is disposed in the outer ring 1 and the syringe flanges 12 engage the flange slots 302 on the inner ring 2, the syringe 13 may be rotated and thus cause rotation of the inner ring 2 and the magnet 401 relative to the outer ring 1.

In the case where the injector 15 has a magnetic sensor to determine the load or lock state of the syringe 13, the associated movement of the magnet 401 may make such indication to such a sensor.

In one exemplary method for operating a medical injector system in accordance with this disclosure, a power injector is provided with a ram. The power injector has a faceplate. An adapter is provided. The adapter includes an outer ring having a first end and an inner ring disposed coaxially within the outer ring. The inner ring has a first end including at least one flange slot. A magnet is fixed relative to the inner ring. A syringe is provided having a barrel with a distal end and a proximal end and an interior volume defined therebetween. At least one flange extends from proximal end, and a delivery tip extends from the distal end. The syringe is loaded on the power injector by passing the proximal end of the syringe through the first end of the outer ring, and the at least one flange engages the at least one flange slot. The syringe is rotated to cause rotation of the inner ring and magnet relative to the outer ring.

Prior to loading the syringe on the power injector, the method may include filling the syringe with a fluid for injection.

After loading the syringe on the power injector, the method may include filling the syringe with a fluid for injection.

In the method, the loading may include loading the syringe on the power injector with a plunger engaging the ram. The method may further include driving the ram to push fluid from the syringe.

Engaging the ram may include the use of a ram extension connected to the end of the ram, a ram tip connected to the end of the ram extension opposite the ram, and a cone for supporting the plunger connected to the ram tip opposite the ram extension.

For further example, a syringe load/unload procedure in accordance with this disclosure includes having an outer ring in fixed in position relative to an Original Equipment Manufacture (OEM) faceplate. Orientation for the outer ring is maintained by engagement of a slot in the outer ring with one or more protrusions on the faceplate. An inner ring is moveably coaxially disposed within the outer ring. The inner ring includes the flange slots for accepting flanges on a syringe. The alignment of the outer ring and/or inner ring may be biased with engagement of a spring plunger cooperating with the faceplate or an injector head and a corresponding slot in the outer ring or inner ring. Additionally, rotation of the outer ring or inner ring may be limited a circumferentially extending the radial slot on outer ring or inner ring that interacts with a protrusion, such as a fixed protruding pin, on the faceplate or on the injector head.

For additional example, a magnet positioning procedure in accordance with this disclosure includes having a magnet fixed relative to the inner ring. Movement of the inner ring between a load and an unload position also causes corresponding movement of the magnet. As the magnet is rotated away in such movement, for example from a hall effect sensor associated with the injector, movement of the magnet relative to the sensor may signal to the injector that a syringe is in a particular place or state.

In more example, a syringe retention or lock procedure in accordance with this disclosure includes that the syringe is placed into the syringe adapter, the syringe flanges are placed into the flange slots on the inner ring. The syringe is then rotated, for example 90 degrees clockwise, and the syringe is locked into position with the syringe flanges biased between the flange slots of the inner ring and the ring flanges of the outer ring. This relative positioning of the inner and outer ring may be maintained by an engagement of a spring plunger with the corresponding slot in the outer ring. Additionally, rotation may be limited by the a radial slot formed in the inner ring that interacts with a fixed protruding pin on the injector head.

While principles and modes of operation have been explained and illustrated with regard to particular embodiments, it must be understood, however, that this may be practiced otherwise than as specifically explained and illustrated without departing from its spirit or scope.

What is claimed is:

1. A medical system for injecting a fluid comprising:
   a power injector with a ram for pushing fluid from a syringe, the injector including:
      a faceplate, and
      an adapter for use with a syringe, the adapter engaging the faceplate, the adapter including:
         an outer ring, the outer ring having a first end including a passage configured to receive an end of a syringe having at least one flange,
         an inner ring disposed coaxially within the outer ring, the inner ring including a central opening configured to receive the ram, a first end including at least one flange slot disposed toward the first end of the outer ring, and a second end including a radial slot interacting with a fixed protrusion on the power injector to limit rotation of the inner ring, and
         a magnet fixed relative to the inner ring,
         where when the syringe end is disposed in the outer ring and the at least one flange engages the at least one flange slot, rotation of the syringe causes rotation of the inner ring and magnet relative to the outer ring and
         where the faceplate includes an upper faceplate portion and a lower faceplate portion that together are disposed around the outer ring and retain the adapter to the injector.

2. The system of claim 1 further comprising:
   a syringe having
   a barrel having a distal end and a proximal end and a defining an interior volume therebetween,
   at least one flange extending from the proximal end and configured to fit within the at least one flange slot of the inner ring, and
   a delivery tip extending from the distal end,
   where the ram drives a plunger disposed within the barrel to push fluid from the syringe.

3. The system of claim 2 further comprising:
   a ram extension connected to the end of the ram,
   a ram tip connected to the end of the ram extension opposite the ram, and
   a cone for supporting the plunger connected to the ram tip opposite the ram extension.

4. The system of claim 2 where the inner ring has two flange slots and where the syringe has two flanges extending in opposed directions from the circumference of the barrel, the two flanges disposed in the flange slots.

5. The system of claim 1 where the injector further comprises a faceplate ring that cooperates with the upper faceplate portion and the lower faceplate portion to retain the outer ring within the faceplate.

6. The system of claim 1 where the magnet is fixed relative to second end of the inner ring by a magnet holder.

7. A method for operating a medical injector system comprising:
   providing a power injector with a ram and having a faceplate,
   providing an adapter including
      an outer ring having a first end,
      an inner ring disposed coaxially within the outer ring, the inner ring having a central opening for passage of the ram, the inner ring having a first end including at least one flange slot, and the inner ring having a second end including a radial slot, and
      a magnet fixed relative to the inner ring,
      wherein the faceplate includes an upper faceplate portion and a lower faceplate portion that together are disposed around the outer ring and retain the adapter to the power injector,
   providing a syringe having:
      a barrel having a distal end and a proximal end and a defining an interior volume therebetween,
      at least one flange extending from proximal end, and
      a delivery tip extending from the distal end,
   loading the syringe on the power injector by passing the proximal end of the syringe through the first end of the outer ring, engaging the at least one flange slot with the at least one flange, and
   rotating the syringe to causes rotation of the inner ring and magnet relative to the outer ring, wherein the radial slot interacts with a fixed protrusion on the power injector to limit rotation of the inner ring.

8. The method of claim 7 further comprising, prior to loading the syringe on the power injector, filling the syringe with a fluid for injection.

9. The method of claim 7 further comprising, after loading the syringe on the power injector, filling the syringe with a fluid for injection.

10. The method of claim 7 wherein the loading includes loading the syringe on the power injector with a plunger engaging the ram.

11. The method of claim 10 further comprising:
    driving the ram to push fluid from the syringe.

12. The method of claim 10 wherein engaging the ram includes the use of a ram extension connected to the end of the ram, a ram tip connected to the end of the ram extension opposite the ram, and a cone for supporting the plunger connected to the ram tip opposite the ram extension.

13. An adapter for use with a syringe and a power injector with a moveable ram for pushing fluid from the syringe, the adapter comprising:
    an outer ring having a first end including a passage configured to receive an end of a syringe having at least one flange, the outer ring including a second end having a slot for engagement of a spring protrusion,
    an inner ring disposed coaxially within the outer ring, the inner ring having a central opening configured to receive the moveable ram, the inner ring having a first end including at least one flange slot, and the inner ring includes a radial slot for interaction with a protrusion on an injector head of the power injector to limit rotation of the inner ring, and
    a magnet fixed relative to the inner ring,
    where when the syringe end is disposed in the outer ring and the at least one flange engages the at least one flange slot, rotation of the syringe causes rotation of the inner ring and magnet relative to the outer ring and where the faceplate includes an upper faceplate portion and a lower faceplate portion that together are disposed around the outer ring and retain the adapter to the injector.

14. The adapter of claim 13 where the magnet is fixed relative to the inner ring by a magnet holder.

15. The adapter of claim 13 further comprising a spring plunger engaging a slot in the outer ring for biasing the position of the inner ring.

16. The system of claim 1 wherein the outer ring further includes an annular groove, the annular groove circularly disposed in an outer surface of the outer ring between the first end and the second end for cooperative engagement with the faceplate.

17. The adapter of claim 13 wherein the outer ring further includes an annular groove, the annular groove circularly disposed in an outer surface of the outer ring between the first end and the second end for cooperative engagement with the faceplate.

18. The system of claim 1 wherein the protrusion is a fixed pin on an injector head of the power injector.

19. The system of claim 1 wherein the outer ring includes a second end having a slot for engagement of a spring protrusion on the faceplate of the injector.

20. The system of claim 1 wherein the magnet moves relative to a sensor on the faceplate or an injector head of the power injector.

* * * * *